March 17, 1942. R. B. WISER Plant Pat. 507
PEACH TREE
Filed Dec. 2, 1940
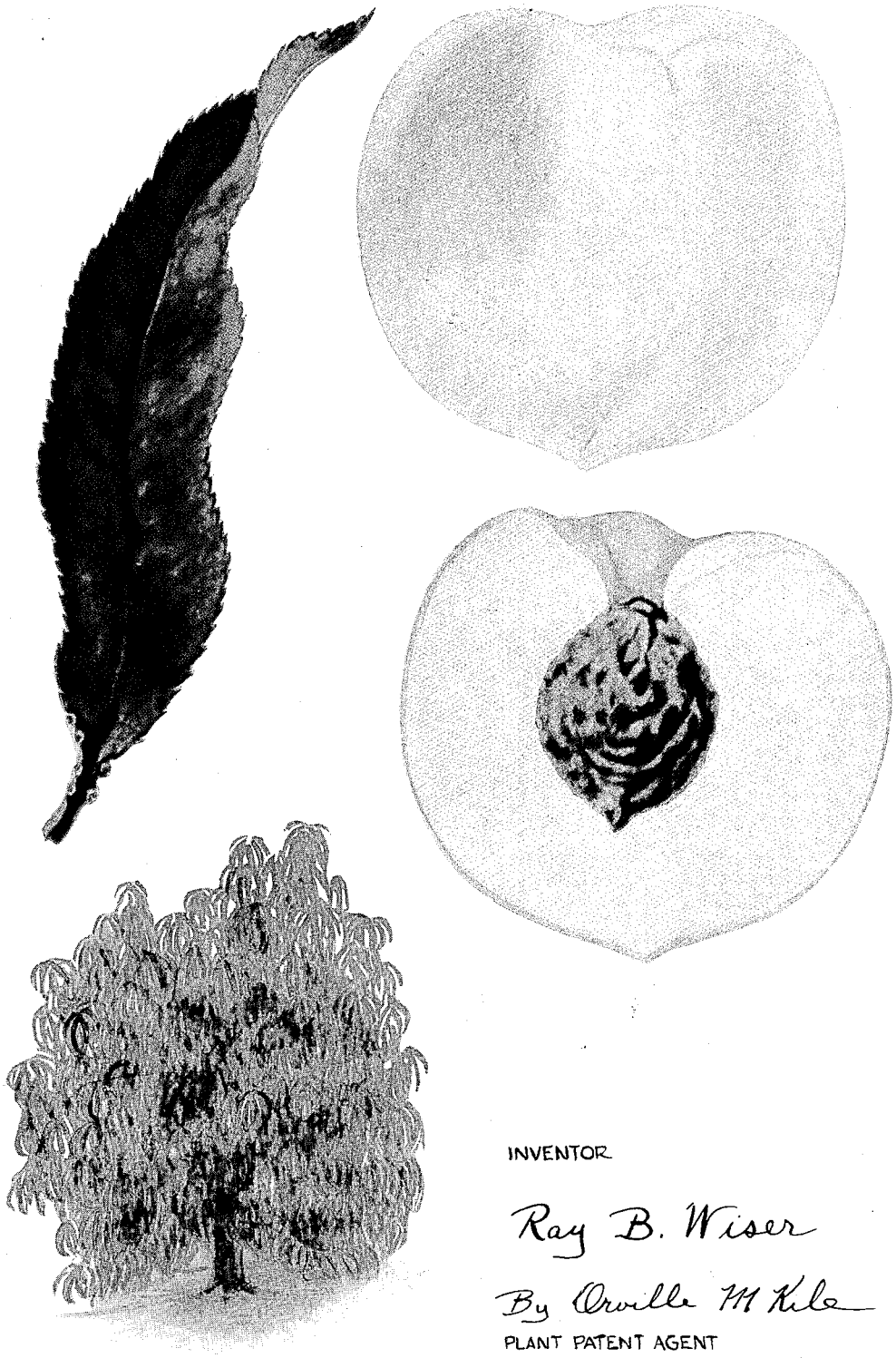
INVENTOR
Ray B. Wiser
By Orville M Kile
PLANT PATENT AGENT Patented Mar. 17, 1942

Plant Pat. 507

UNITED STATES PATENT OFFICE

507

PEACH TREE

Ray B. Wiser, near Gridley, Calif.

Application December 2, 1940, Serial No. 368,261

1 Claim. (Cl. 47—62)

My invention relates to a new and distinct variety of peach tree and is an improvement in peach trees producing late-maturing yellow cling peaches of the type used for canning purposes.

One of the outstanding features of the tree is its willowy, drooping growth which enables it to sustain a much larger crop without breaking than would otherwise be possible.

In outside appearance and many other features the fruit of this new variety is more like that of the Lovell (one of its parents) than any other peach. But the new peach is a cling, whereas the Lovell is a freestone. The new fruit has a distinctive Lovell flavor and aroma, which is notably absent from clingstone peaches in general.

Another feature of this new variety is the tenacity of its fruit to the tree, this quality affording a longer picking season than is usual.

This new variety originated by me in my orchards near Gridley as a seedling resulting from a controlled cross of Sims into Lovell. I observed it for several years after it first came into bearing. Then I planted five acres with asexually reproduced plants of this variety which have since come into bearing with no noticeable variation from the original, thus showing that the distinctive qualities of the variety are firmly fixed.

The original paintings accompanying this application show; (1) A cross section view and a full side view of the fruit in full colors and slightly enlarged size; (2) a leaf in natural color, and slightly enlarged size, showing glands at the base of the leaf; and (3) a small water-color sketch showing the drooping growth of the leaves and the tree.

Following is a detailed description of typical specimens of this new variety of peach tree and their fruit.

*The tree*

Growth: Thrifty and vigorous.

Trunk: Stocky.

Branches: Willowy and strong, enabling them to bend under heavy loads without breaking.

Leaves:

*Shape.*—Long and narrow. Edge finely serrated.

*Size.*—Averages 6½ inches long by 1⅜ inches wide.

*Position.*—Closely spaced on branches, with short petioles which bring the leaves close to the branches. At about 4 inches from tip of branch they are less than half an inch apart and progressively closer together toward the tip of branch. This position of the leaves contributes greatly to the willowy effect of the tree.

*Aspect.*—Lightly veined; relatively thin.

*Glands.*—Five to seven; prominent; quite globose, having a slight indentation in center of top.

*Color.*—Medium green.

Blossoms: Pale pink, somewhat lighter than most peach blossoms, also slightly smaller than most other peach blossoms. The variety blooms slightly earlier than many others—about the same time as the Sims.

Disease resistance: Very resistant to diseases common to peaches, particularly to mildew.

Maturity: Fruit is late-maturing—slightly later than either of its parents. Its picking season is longer than most varieties because of the tenacity of its fruit to the stem.

*The fruit*

Shape: Oblate, almost round more symmetrical than the usual cling.

*Suture.*—Very shallow.

*Cavity.*—Deep but not wide.

*Tip.*—Notably small and flattened.

Size: Approximately 2⅜ inches in axial diameter by 2½ inches in transverse diameter. Uniform.

Skin:

*Color.*—Orange yellow with slight red blush on upper portion of one cheek.

*Texture.*—Thin and tough, similar to that of freestones.

*Pubescence.*—Average amount.

Flesh:

*Texture.*—Firm but juicy. Few fibers.

*Color.*—Clear yellow without red around the pit.

*Flavor.*—Sweet; much like Lovell.

*Aroma.*—Slight but distinct.

Stone:

*Type.*—Clinging.

*Size.*—Small.

*Shape.*—Almost round.

Canning and shipping qualities: Superior.

Having thus disclosed my invention, I claim:

The new and distinct variety of late-maturing peach tree herein described, characterized particularly by its vigor and heavy bearing ability; its willowy growth, the effect of which is greatly increased by its long slender leaves which are close-set on the branches; its prolonged harvesting season produced by the tenacity of its fruit to the tree; the symmetry and uniformity of size of its fruit; its great degree of disease resistance; and its clingstone fruit having outer appearance and flesh similar to that of the freestone Lovell fruit, substantially as shown and described.

RAY B. WISER.